(12) United States Patent
Frayling (10) Patent No.: US 8,440,403 B2
(45) Date of Patent: May 14, 2013

(54) APPARATUS AND METHOD

(75) Inventor: Cameron Frayling, Leamington Spa (GB)

(73) Assignee: Base4 Innovation Limited, Cambridge (GB)

( * ) Notice: Subject to any disclaimer, the term of this patent is extended or adjusted under 35 U.S.C. 154(b) by 0 days.

(21) Appl. No.: 13/459,612

(22) Filed: Apr. 30, 2012

(65) Prior Publication Data

US 2012/0237940 A1    Sep. 20, 2012

Related U.S. Application Data

(62) Division of application No. 12/676,472, filed as application No. PCT/GB2008/050783 on Sep. 4, 2008.

(30) Foreign Application Priority Data

Sep. 4, 2007   (GB) .................................... 0717150.7

(51) Int. Cl.
*C12Q 1/68*   (2006.01)
*G01N 21/64*   (2006.01)
*B82Y 15/00*   (2011.01)

(52) U.S. Cl.
USPC ... 435/6.1; 435/283.1; 435/288.4; 435/288.7; 422/68.1; 422/82.08; 977/704; 977/733; 977/781; 977/924

(58) Field of Classification Search .................. None
See application file for complete search history.

(56) References Cited

U.S. PATENT DOCUMENTS

| | | | |
|---|---|---|---|
| 4,873,034 A | 10/1989 | Kono et al. | |
| 6,267,872 B1 | 7/2001 | Akeson et al. | |
| 6,972,173 B2 | 12/2005 | Su et al. | |
| 6,982,165 B2 | 1/2006 | Yamakawa et al. | |
| 7,238,477 B2 | 7/2007 | Su et al. | |
| 2002/0182627 A1 | 12/2002 | Wang et al. | |
| 2003/0036204 A1* | 2/2003 | Stark et al. | 436/172 |
| 2003/0207326 A1 | 11/2003 | Su et al. | |

(Continued)

FOREIGN PATENT DOCUMENTS

| DE | 101 57 070 A1 | 6/2003 |
|---|---|---|
| DE | 103 61 927 A1 | 7/2005 |

(Continued)

OTHER PUBLICATIONS

International Search Report and Written Opinion of the International Searching Authority issued Feb. 5, 2009 in corresponding International Application No. PCT/GB2008/050783.

(Continued)

*Primary Examiner* — Betty Forman
(74) *Attorney, Agent, or Firm* — Wenderoth, Lind & Ponack, L.L.P.

(57) ABSTRACT

An apparatus for investigating a molecule comprising a channel provided in a substrate, a metallic moiety capable of plasmon resonance which is associated with the channel in a position suitable for the electromagnetic field produced by the metallic moiety to interact with a molecule passing therethrough, means to induce a molecule to pass through the channel, means to induce surface plasmon resonance in the metallic moiety; and means to detect interaction between the electromagnetic field produced by the metallic moiety and a molecule passing through the channel. Methods of investigating molecules are also provided.

15 Claims, 4 Drawing Sheets

U.S. PATENT DOCUMENTS

| | | | |
|---|---|---|---|
| 2005/0019784 A1* | 1/2005 | Su et al. ............................ 435/6 |
| 2005/0023156 A1 | 2/2005 | Ramsey et al. |
| 2005/0084912 A1 | 4/2005 | Poponin |
| 2005/0148064 A1 | 7/2005 | Yamakawa et al. |
| 2006/0066848 A1 | 3/2006 | Frankel |
| 2006/0147927 A1 | 7/2006 | Geddes et al. |
| 2006/0192115 A1 | 8/2006 | Thomas et al. |
| 2006/0238767 A1 | 10/2006 | Chen et al. |
| 2007/0153284 A1 | 7/2007 | Glazier et al. |
| 2007/0247620 A1 | 10/2007 | Koo |
| 2007/0273884 A1 | 11/2007 | Matsushita et al. |
| 2007/0275383 A1* | 11/2007 | Vocanson et al. ................. 435/6 |
| 2008/0025875 A1 | 1/2008 | Martin et al. |
| 2008/0037022 A1 | 2/2008 | Nishikawa et al. |
| 2008/0218761 A1 | 9/2008 | Nishikawa et al. |
| 2008/0239307 A1 | 10/2008 | Talley et al. |

FOREIGN PATENT DOCUMENTS

| | | |
|---|---|---|
| WO | 2005/078415 | 8/2005 |
| WO | 2005/095927 | 10/2005 |
| WO | 2006/050257 | 5/2006 |
| WO | 2007/011389 | 1/2007 |
| WO | 2007/039852 | 4/2007 |

OTHER PUBLICATIONS

Antoine Lesuffleur et al., "Periodic nanohole arrays with shape-enhanced plasmon resonance as real-time biosensors," Applied Physics Letters, Jun. 13, 2007, pp. 243110-1-243110-3, XP002511474.

Hagan Bayley et al., "Stochastic sensors inspired by biology," Nature, vol. 413, Sep. 13, 2001, pp. 226-230, XP002511333.

J. Aizpurua et al., "Optical Properties of Gold Nanorings," Physical Review Letters, vol. 90, No. 5, Feb. 7, 2003, pp. 057401-1-057401-4, XP002511334.

J. B. Heng et al., "The Electromechanics of DNA in a Synthetic Nanopore," Biophysical Journal, vol. 90, Feb. 2006, pp. 1098-1106, XP002511335.

Toshihiro Nakamura et al., "Enhancement of Dye Fluorescence by Gold Nanoparticles: Analysis of Particle Size Dependence," Japanese Journal of Applied Physics, vol. 44, No. 9A, Sep. 8, 2005, pp. 6833-6837, XP002511336.

Chuen Ho et al., "Electrolytic transport through a synthetic nanometer-diameter pore," Proceedings of the National Academy of Sciences of the United States of America, vol. 102, No. 30, Jul. 26, 2005, pp. 10445-10450, XP002511337.

M. Caterina Netti et al., "Confined Surface Plasmons in Gold Photonic Nanocavities," Advanced Materials, vol. 13, No. 18, Sep. 14, 2001, pp. 1368-1370, XP002511338.

S. O. Kucheyev et al., "Surface-enhanced Raman scattering on Nanoporous Au," Applied Physics Letters, Jul. 31, 2006, pp. 053102-1-053102-3, XP002511475.

Liu et al, "Biosensing based upon molecular confinement in metallic nanocavitiy arrays," Nantechnology, 2004, 15:1368-1347.

Stefan A. Maier, "Plasmonics: Fundamentals and Applications", Springer, 2007.

Japanese Office Action issued Jan. 29, 2013 in corresponding Japanese Application No. 2010-523597 (English language translation provided).

* cited by examiner

APPARATUS AND METHOD

This application is a Divisional of application Ser. No. 12/676,472, filed Oct. 25, 2010, which is the National Stage of International Application No. PCT/GB2008/050783, filed Sep. 4, 2008.

APPARATUS AND METHOD

The present invention relates to apparatus and methods for investigating molecules, in particular biological molecules such as nucleic acids or proteins. The apparatus and methods are concerned with application of nanoscale technology to the problems of rapid and detailed analysis of these molecules. In one aspect the present invention relates to apparatus and methods of sequencing nucleic acids.

The ability to rapidly sequence nucleic acids remains of paramount importance in biology. Although the entire sequences of many genomes (including human) are now known, and many more are becoming available, the remains a need to obtain sequence data for many reasons. Current sequencing technologies are primarily based on the Sanger ("dideoxy") technique and are laborious and slow. Methods involving the detection of the incorporation of single nucleotides by a polymerase are intrinsically limited to the relatively low speed at which a polymerase can synthesise a complementary DNA strand. Currently the maximum sequencing rate for a single sequencing device is approximately 1 base/second; though an improvement over conventional Sanger sequencing techniques, this is still very slow.

Methods through which DNA is sequenced via detecting changes of current as DNA passes through a conducting pore have been proposed. Although such methods have a high theoretical maximum speed of detection, to date relatively low detection rates have been achieved and it seems likely that without extensive modification to the overall design or the use of conducting labels, the limit of detection will remain low.

Nanotechnology, like biology, is an area which is rapidly developing and is leading to novel approaches and materials for the manipulation and analysis of molecules. Nanotechnologists are now able to produce and manipulate materials down to the sub-nanometer scale. This provides the potential for the development of devices or techniques with new and previously unconsidered potential. However, while nanotechnology has found utility, for example, in the electronics industry, it has not yet been widely harnessed in the field of biology.

Plasmon resonance is a phenomenon whereby plasmons on a metallic surface are excited by light incident upon the surface. Plasmon resonance is used in a number of conventional analytical machines, such as Biacore®. Where plasmons on a planar surface are excited the term surface plasmon resonance (SPR) is used, and where a nanometer sized particle is excited the term localised surface plasmon resonance (LSPR) is often used to differentiate this aspect of the phenomenon. When a small metallic particle is irradiated by light, the oscillating electric field causes the particle's electrons to oscillate coherently. The collective oscillation of these electrons is called the dipole plasmon resonance. The collective oscillation in the electron cloud produces an intense, highly localised electromagnetic field (EMF). In order to produce these collective oscillations, the correct excitation wavelength must be used. This wavelength will depend on both the size and shape of the metal particle or nanostructure being excited.

It has been discovered that by using highly localised SPR achievable using nanotechnological techniques, the structure of biological molecules can be investigated at the nanometer scale.

According to the present invention there is provided an apparatus for investigating a molecule comprising:
- at least one channel provided in a substrate, the channel being suitable for the passage of the molecule therethrough;
- at least one metallic moiety capable of plasmon resonance, the at least one metallic moiety being associated with said channel in a position suitable for the electromagnetic field produced by the metallic moiety to interact with the molecule passing therethrough;
- means to induce a molecule to pass through the channel;
- means to induce surface plasmon resonance in the metallic moiety; and
- means to detect interaction between the electromagnetic field produced by the metallic moiety and a molecule passing through the channel.

Suitably the apparatus comprises two reservoirs: a first reservoir suitable to receive a sample comprising the molecule to be investigated, and a second reservoir suitable for the molecule to pass into once it has passed through the channel. Suitably the two reservoirs are separated from each other by the substrate, and the molecule must pass through the at least one channel to pass from the first reservoir into the second reservoir. Thus the substrate could be considered to be a membrane or diaphragm separating the two reservoirs.

Generally the dimensions of the channel should be suitable for a molecule to be investigated to pass through the channel, and such that the molecule is constrained to pass suitably close to the metallic moiety such that an interaction between the molecule and the localised EMF produced by the metallic moiety occurs. The channel should generally also have suitable dimensions such that only one molecule can pass through the channel at a time.

Generally it is preferred that the channel is an aperture, though it is possible that other forms of channels such as slots or grooves provided in a substrate may also be suitable.

The aperture may have any suitable shape, although a circular or approximately circular aperture is envisaged as being most convenient.

The aperture (or channel) may have a diameter of from approximately 0.5 nm to 100 nm preferably 50 nm or less, especially 30 nm or less. Although the term diameter is used, it should be understood that it is not meant in a strict geometrical sense and may, for example, apply to the smallest dimension of a non-circular aperture or channel.

Often small apertures in a substrate are referred to as "pores", and this term may be used throughout the specification and should be construed accordingly.

Where the molecule to be investigated is a nucleic acid, the smallest aperture through which single-stranded nucleic acid will pass is approximately 1 nm. Double-stranded nucleic acids will pass through an aperture of approximately 2 nm or greater [see Heng J. B. et al. Biophysical Journal (2006), 90, 1098-1106].

Accordingly, where a single stranded nucleic acid is to be investigated, it is preferable that the aperture should be from 1 nm to 100 nm in diameter, preferably 1 nm to 30 nm, especially 1 to 10 nm, particularly 1 to 5 nm. For double stranded nucleic acid the aperture should be from 2 nm to 100 nm in diameter, preferably from 2 nm to 30 nm, especially from 2 nm to 4 nm.

The channel may be formed of any suitable substance. It may be organic or inorganic.

In one embodiment the aperture may be formed from an "organic" pore, i.e. a pore derived from a naturally occurring structure, for example a protein having a pore such as α-haemolysin or the organic pore found in the outer membrane of mitochondria.

Alternatively the aperture could be provided by a gel conventionally used for the manipulation of nucleic acid or other biological molecules, such as agarose or polyacrylamide.

Alternatively, the aperture could be engineered in a substrate such as a film formed from silicon nitride or other such material. See, for example, Ho C. et al., PNAS (2005), 102(30) 10445-10450 which discusses methods of forming nanometer diameter pores from silicon nitride.

The aperture could also be formed from a nanoporous material such as porous gold, a colloidal crystal, colloidal cavities, metal toroids etc. Netti et al. describe the formation of gold nanocavities and their ability to form surface plasmons [see Netti M. C. et al. Advanced Materials (2001), 13(18), 1368-1370]. Aizpurua O. et al. describe the formation of gold nanorings [see Aizpurua et al. Physical Review Letters (2003), 90(5), 057401-1-057401-4]. Lesuffleur et al. discuss gold nanopore arrays with enhanced plasmon resonance [Lesuffleur A. et al., Applied Physics Letter (2007), 90, 243110]. Where the aperture is itself formed from a metallic substance capable if exhibiting LSPR, then it will be apparent that a separate metallic moiety may not be required.

Means for nano-engineering to produce a variety of suitable structures for the present invention are well known, but this is also a rapidly developing field of technology. As such, it is expected that novel technologies and materials suitable for forming channels in a substrate as required by the present invention will be developed in the future; such technologies are within the scope of the present invention.

It is generally preferred that the apparatus comprises a plurality of apertures passing through the substrate. The apertures could be arranged in an array where the position of each aperture is controlled; this is particularly convenient where nano-engineering is used to form apertures in a substrate. Alternatively, the apertures could be scattered across the substrate without control over their position.

The metallic moiety must be able to form surface plasmons and thus form a localised EMF in the vicinity of the moiety. Any material which is suitable to achieve this function is suitable for use in the metallic moiety. Gold, silver, copper and aluminium metals have been found to have desirable properties in terms of plasmon formation and propagation, and thus it is generally preferred that the metallic moiety is formed predominantly or entirely from one or more of these metals.

Nanotechnology allows the formation of gold or silver particles in essentially any shape. Shape can have a substantial effect on the EMF produced by a particle [see Mock J. J. et al., Journal of Chemical Physics, 116(15), 6755-6759].

A spherical or substantially spherical (e.g. a sphere or spheroid) particle has suitable properties and thus forms a suitable embodiment of the metallic moiety. It has been found that spherical metal particles having a diameter of from 50 nm to 150 nm in diameter are especially suitable due to high levels of fluorescence enhancement [see Nakamura and Hayashi, Japanese Journal of Applied Physics, 44(9A), 6833-6837].

In an alternative embodiment an annular metallic moiety may be used. Such an annular moiety has certain benefits; it has been shown that the EMF within a ring is strong and is relatively constant across the inner area defined by the ring [see Aizpurua et. al., ibid]. Where the metallic moiety is a ring, it will be obvious that the ring could itself form the aperture through which the molecule will pass. Methods of manufacturing such nano-rings are set out in Aizpurua et al.

Other shapes such as polygonal prism or other multi-sided shapes may also be suitable.

For the sake of clarity it is pointed out that there may be more than one metallic moiety associate with a particular channel, and that more than one type of metal may be used. Indeed, it may be desirable to use two or more metallic materials such that a region of maximal EMF is produced as a result of combination of the separable EMFs of each moiety. This may give rise to extremely high EMF values in highly localised areas.

It is generally important that the metallic moiety is arranged in a position such that it will interact with a molecule passing through the pore, but is spaced sufficiently from the pore to prevent or mitigate quenching of a signal emitted from the molecule. This can be achieved in a number of ways. The channel may be shaped and sized such that a molecule passing through it is constrained in a position such that it does not get too close (thus avoiding quenching), or too far away (thus ensuring interaction) from the metallic moiety—this is especially suitable when the pore itself has no quenching activity. Alternatively, control means may be used to guide the molecule such that it does not get too close to the metallic moiety.

Typically the surface of the metallic moiety should be positioned to be 50 nm or less from the molecule as it passes through the channel, preferably 30 nm or less, especially 10 nm or less.

The means to induce a molecule to pass through the channel may be one or more of means to induce electrophoresis, a micro-fluidics device, or a laser trapping device. However, any other means suitable to induce the molecule to move to and/or through the channel may also be suitable.

The apparatus may comprise control means to control the passage of the molecule towards, into and/or through the aperture. The control means may be adapted to control one or more of the velocity, direction, position or conformation of the molecule.

The type of control means will vary depending on the type of molecule to be investigated and the type of control required. Where sequencing of nucleic acid is required, it is important that the speed of passage of the linear nucleic acid molecule through the channel is controlled. For sequencing it is also desirable that the nucleic acid molecule is held in a linear conformation.

In one embodiment the control means may comprise a porous matrix through which the molecule passes, the porous matrix lying immediately adjacent to the entrance to the channel. Where a porous matrix is used, it is convenient if the molecule is induced to pass through the matrix via electrophoresis. The properties of the porous matrix in combination with the electrophoresis conditions serve to allow fine control of the movement of the molecule (e.g. nucleic acid) through the matrix and into the channel. Accurate control of the speed of movement of a nucleic acid through a gel can be achieved. An additional advantage of electrophoresis though a porous matrix is that the conformation of a linear molecule is drawn out into an elongated, linear form which is particularly suitable for sequencing. A suitable porous matrix may be formed from convention materials used for manipulating nucleic acids and proteins, such a polyacrylamide or agarose. Alternatively, other nano-porous materials may also be suitable.

The control means described above is well suited for the control of nucleic acids and other linear molecules. Other molecules may require a different level of control, or the degree of control may be higher or lower.

It should be noted that the means to induce a molecule to pass through the channel and the control means may be provided by the same means. For example electrophoresis in a liquid medium alone may be suitable for controlling molecules where accurate control of conformation and velocity is not required. Alternatively, laser trapping may be used to accurately control the movement of a molecule toward and into the channel.

The means to detect interaction of the metallic moiety and the molecule may of course be any suitable device which can detect the interaction between the localised EMF produced by the moiety and the molecule in close proximity to it. Suitable means may include means to detect fluorescence or means to detect Raman scattering.

Suitable means to detect fluorescence include any device which is sensitive enough to detect photons emitted from a fluorophore passing through the region of EMF. Suitable devices include a photomultiplier or an avalanche photodiode. Fluorescence is suitable to detect inherently fluorescent molecules or molecules which have been labelled with a fluorophore.

Suitable means to detect Raman scattering include a Raman spectrometer. Raman scattering may be used to detect unlabelled and non-fluorescent molecules. Techniques to detect Raman scattering are well known in the art. Detection using Raman scattering in the present invention are based on the phenomenon of surface enhanced Raman spectroscopy [see for background Jeanmaire, David L.; Richard P. van Duyne (1977). "Surface Raman Electrochemistry Part I. Heterocyclic, Aromatic and Aliphatic Amines Adsorbed on the Anodized Silver Electrode". Journal of Electroanalytical Chemistry 84: 1-20.]

In many embodiments it may be preferred if a method of detection is used which does not rely on labelling of the molecule. This simplifies the preparation of the sample to be investigated, and also does not require the presence of a label which may interfere with the passage of the molecule through the channel.

In a further aspect the present invention provides a method for investigating a molecule comprising the steps of;
provindg a fluid sample comprising a molecule to be investigated;
inducing said molecule to pass through a channel provided in a substrate, the channel having an associated metallic moiety which is induced to have plasmon resonance;
detecting interaction between the electromagnetic field produced by the metallic moiety and the molecule as it passes through the channel.

Preferably the molecule is a biological molecule, e.g. a nucleic acid or a protein/peptide. Linear molecules such as nucleic acids or linear proteins/peptides are particularly suitable for investigation using the present method. Single-stranded nucleic acid is especially suited for investigation using the present method.

In a preferred embodiment the method is a method of sequencing a nucleic acid.

However, the method may also be used for investigation of other sorts of molecules, and need not be used for sequencing. The use of the method for counting individual molecules in a sample, and mapping of markers on linear molecules are envisaged as being amongst other potential uses.

It may be preferred, though it is not essential, that the molecule comprises a label which interacts with the metallic moiety. Accordingly, the method may further comprise the step of labelling the molecule with a label which will interact with said metallic moiety.

Suitable labels include fluorophores. Fluorophores are well known in the art in relation to fluorescent labelling of all types of biological molecules. In the present invention it is important that the fluorophore is small enough that it does not inhibit passage of the labelled molecule through the channel. Typically the fluorophore will have a effective size of 2 nm or less, and preferably a dye molecule measuring less than 1 nm in any dimension.

Examples of suitable fluorophores include Rose Bengal, Alexa Fluor 488 $C_5$-maleimide, Alexa Fluor 532 $C_2$-maleimide and Rhodamine Red $C_2$-meleimide, and Rhodamine Green. These fluorophores can each be used to label the bases of nucleic acids using techniques known in the art.

Suitably the molecule is a nucleic acid in which a substantial proportion or all of a particular base has been labelled. In a preferred embodiment a substantial proportion or all of one or more bases in the molecule are labelled, each type of base having a label with an individually identifiable emission spectrum. In an especially preferred embodiment all, or substantially all the bases are labelled, each type of base having a label with an individually identifiable emission spectrum. High density labelling of nucleic acid is discussed in Tasara et al., Nucleic Acids Research, 2003, 31(10), 2636-2646.

It is important that a fluorophore selected as a label is capable of interacting with the EMF produced by the metallic moiety. It is a routine matter to match a fluorophore to a metallic moiety of particular properties. In general for good interaction between the metallic moiety and the fluorophore, it is preferred that the fluorophore has an emission peak at slightly lower energy than the localised surface plasmon resonance peak of the metallic moiety, i.e. the fluorophore emission peak is slightly red shifted from the LSPR peak. Red shifts of from approximately 20 to 150 meV are suitable, preferably from approximately 40 to 120 meV [see Chen et al., Nano Letters (2007), 7(3), 690-696].

According to a further aspect, the present invention provides a substrate suitable for use in an apparatus for investigating a molecule comprising:
at least one channel provided in the substrate, the channel suitable for the passage of a molecule therethrough; and
at least one metallic moiety suitable to have plasmon resonance induced therein, the at least one metallic moiety being associated with said channel in a position such that the electromagnetic field produced by the metallic moiety is able to interact with a molecule passing therethrough.

Further details of preferred substrates are set out above.

Embodiments of the invention will now be described, by way of non-limiting examples, with reference to the accompanying drawings in which.

BACKGROUND

When a small spherical metallic particle is irradiated by light, the oscillating electric field causes the particle's electrons to oscillate coherently. The collective oscillation of these electrons is called the dipole plasmon resonance. The collective oscillation in the electron cloud produces an intense, highly localised electromagnetic field (EMF). In order to produce these collective oscillations, the correct excitation wavelength must be used. This wavelength will depend on both the size and shape of the metal particle being excited.

The correct wavelength for a particular particle can easily be determined experimentally or, for certain shapes, may be predicted using known modeling techniques.

It has been shown in [1] that the EMF produced by the plasmon resonance of metal colloids such as gold or silver nanoparticles can be used to excite commonly used fluorescent labels such as Cy5 and Rose Bengal, amongst others. These experiments involved placing gold or silver nanoparticles on a surface and positioning the fluorophores such that they benefit from the enhanced EMF. This results in what is called metal enhanced fluorescence (MEF).

When a fluorophore is placed near a metal particle exhibiting plasmon resonance, the fluorophore benefits from both the localised EMF and from a less-well understood phenomenon in which the fluorescent lifetime is decreased. A similar phenomenon occurs when the Raman scattering of a molecule is examined. Where the molecule if in close proximity to a metallic particle exhibiting localised surface plasmon resonance a dramatic increase in the level of Raman scattering is observed.

As the maximum photon emission of a fluorophore is determined by its quantum yield and fluorescent lifetime, a shorter fluorescent lifetime results in higher photon emission. A fluorophore having a 90% quantum yield and a fluorescent lifetime of 2.5 ns could emit a maximum of 360 million photons/s. In reality, fluorescent dyes can emit several million photons before deteriorating.

By inducing a highly localised enhanced EMF, such as has been demonstrated using gold and silver colloidal arrays, [1,2] as well as in colloidal nanocrystals [3], photonic crystal nanocavities [4], metal nanorings [5] and porous thin metal films [6] and positioning a fluorophore such that it will benefit from it, MEF can be induced and the fluorophore detected, or alternatively Raman scattering detected.

If a device is made such that there is a region in space where only one fluorophore may benefit from MEF at any given time, the position of that fluorophore can be known. By arrangement of a plasmonic structure (e.g. a metallic moiety) around or adjacent to an aperture (pore), a fluorescent particle can be oriented such that it passes through an area of maximum fluorescent enhancement (MaxFE). Suitable pores include: gels (commonly used to confine polynucleotides), organic pores such α-haemolysin, solid state pores such as can be made in silicon nitride, nanoporous materials such as porous gold, colloidal crystals, colloidal cavities, metal toroids, or any other pore less than 10 nm in diameter and preferentially less than 5 nm in diameter, especially between 1.5 and 2.5 nm.

Given the following:
the EMF between two plasmon resonating surfaces increases when the distance between them decreases,
that proximity to a plasmon resonating surface also diminishes the fluorescent lifetime of the fluorophore,
that the distances between these surfaces can be made less than 5 nm,
and that colloids, porous thin films, 2D crystal arrays, and other nanostructures can made less than 2 nm in size,
it is reasonable to assume that maximum photon emission can be made to occur in an extremely small region.

In a similar way, particular properties of a molecule, or regions within a molecule, can be identified by characteristic patterns of Raman scattering. This, as with the identification of the location of a particular fluorophore, the position of a particular feature having an identifiable Raman spectrum can be identified by its proximity to the plasmonic structure.

If an ion is induced to pass through a pore by means of, for example microfluidics or electrophoresis, it can be made to pass through this area of MaxFE such that detection of a single ion-fluorophore conjugate, or a region having a particular Raman spectrum can be detected.

By inducing a fluorescently labelled charged ion such as a protein to pass through a nanopore such that only one ion may travel through the pore at once, quantification of those ions would be possible as follows:

Given two identical fluorescent particle/ion conjugates, as the first passes through the pore and enters the confined EMF, the fluorophore will begin to emit photons. As the fluorophore moves closer to the region of MaxFE, an increasing number of fluorophores are emitted. As photon emission is directly related to the intensity of the EMF, which in turn increases exponentially as the distance to the region of MaxFE decreases, the photon emission will also increase exponentially, producing a photon emission peak in the region of MaxFE and decreasing as the conjugate moves away from the area of MaxFE. The second identical fluorescent particle will produce the same pattern of photon emission. So long as peak photon emission occurs in a discrete region with a thickness less than the distance between the two fluorophore/ion conjugates, the fluorescence produced by these two fluorophores can be differentiated.

Should the two conjugates be spaced so closely together (less than 0.5 nm) that individual detection would be difficult, the presence of more than one fluorophore in the area of MaxFE could be determined by photon emission. Two identical fluorophores exposed to equal EMF strengths should emit roughly twice as many photons/s as a single fluorophore. Given that a region of MaxFE can contain two, three or more conjugates, if the speed at which they travel through the EMF is known, quantification of the number of conjugates which pass through the EMF can be achieved.

By creating two chambers separated by a barrier which ensures that ions could only pass from one side to the other via a pore, the ions which can be induced to migrate could be quantified regardless of whether the region of MaxFE can contain two, three or more conjugates so long as that number has been determined.

Labelling of Nucleic Acids

Fluorescent labels are commonly incorporated into the both single stranded (ss) and double stranded (ds) polynucleotides DNA and RNA. There are many well-established methods for incorporating fluorescent labels into DNA and by careful choice of both DNA polymerase and fluorescently modified nucleotide, it has been shown [7] that it is possible to fluorescently label all of one or more of the four bases (CGTA). The distances between nucleotides in dsDNA and dsRNA is known to be 0.34 nm, while in ssDNA and ssRNA, the polymers can be in linear conformation, allowing the maximum spatial separation to be greater—although the exact distance varies between 0.5 and 1 nm depending on the stretching force imposed [8].

The Sequencing Process

It is known that precise control of the speed at which a single strand of DNA passes through an organic pore such as a-haemolysin [10] or a solid-state pore in silicon nitride can be achieved [8,9]. By labelling a polynucleotide such that all of one or more of its bases are fluorescently labelled and inducing that polynucleotide by microfluidics, electrophoresis or some other means to pass through an EMF at a known speed such that the nucleotides pass through a region of MaxFE able to contain at least one fluorescently labelled nucleotide, the position of the labelled nucleotides along the DNA fragment can be determined.

A complete polynucleotide sequence could be assembled in the following way:

Assuming all of one base will be labelled at a time, four PCR reactions can be performed in which in each, all of the C, T, G, or A nucleotide bases are fluorescently labelled. The strands are then denatured-forming ssDNA or ssRNA. Each strand is then induced to pass through a nanopore at a known speed and through an area of MaxFE able to contain a known number of nucleotides. As the labelled nucleotides pass through the EMF, their positions can be determined relative to the other labelled nucleotides—providing a distance map for each of the four identical but differently labelled polynucleotides. These four distance maps can then be easily assembled into a complete polynucleotide sequence.

Whole Genome Sequencing

In order to sequence a genome using this method, fluorescently labeled random primers, such as are available for whole genome amplification, could be used. The sequence of these primers would be known and the fluorescent label could serve to indicate the 5' or 3' orientation of the DNA fragment as it passes through the pore. The labelled primer would also serve as an initial reference point from which the distance map of the labelled nucleotides could be related. Preferentially, all of more than one of the four bases would be fluorescently labeled and fluorescent labels with different emission spectra would be used to differentiate these bases. More than one fluorescent label spectra could also be used to label all of one type of base providing the labels had distinct max emission spectra.

These DNA fragments could then be induced to pass through the pore as described above at a rate determined by the photon emission. Using the dye Cy5, photon emission rates for MEF of between 3 and 9 million photons/s have been obtained [1]. This could allow DNA to pass through at a rate of slightly less than one million nucleotide bases per second per nanostructure. An array of nanostructures would allow this speed to be multiplied by the size of the array. As these primers are random and the position of the distance maps for the DNA fragments within the genome is not known, whole genome assembly software such as is used for whole shotgun sequencing would be required for accurate alignment and assembly.

Advantages of the Present Invention

The present invention provides a variety of advantages over other methods of DNA sequencing as well as other methods of single molecule detection:

The invention allows enhanced single molecule detection.
The invention can be used to determine the position and speed of single molecules.
Although PCR can be used to fluorescently label single molecules, the present apparatus and method is not reliant on chemical or enzymatic reactions.
The apparatus can be arrayed such that tens, hundreds, thousands or millions of these nanostructures can be in operation at once.
DNA sequencing using the method outlined above would be extremely fast. The cost of sequencing using this method would be limited to the cost of no more than four PCR reagents such as fluorescent labels, nucleotides, polymerases and other minor consumables.

Methods of Construction

The heart of the invention lies in inducing a single molecule to pass through a highly localised EMF in a controlled manner and detecting interaction between the molecule and the EMF. There are many well-researched methods of controlling both proteins and polynucleotides including gels, organic pores, solid state pores, attachment to beads, and immobilisation on a surface. This allows a wide range of devices to be constructed which could control a single molecule such as a protein or a DNA fragment such that it could be made to pass through a highly localised EMF.

The present invention allows any surface to be used so long as the plasmon resonance induced by an incident EMF will induce MEF in a fluorescently labeled single molecule or SERS, and that single molecule can be induced to pass through an area of MaxFE.

The present invention allows any means of inducing a single molecule to pass through a region of MaxFE including microfluidics, electrophoresis, or laser trapping.

Where fluorescence is the chosen method of detection, the present invention allows any fluorescent label to be used which will fluoresce at the frequency of maximum plasmon resonance of the surface being used. Ideally, the fluorescent label will have a high quantum yield, low fluorescent lifetime, low molecular weight, and be easily incorporated by a polymerase. Preferably, the nucleotides themselves are intrinsically fluorescent.

SERS has the advantage that no labeling is required, but rather the specific Raman spectrum of features of the molecule to be identified should be known.

These characteristics allow for the invention to be engineered in at least three general ways, each of which having distinct advantages:

The use of an "organic" pore to control a single molecule allows gold nanoparticles to be covalently bound either to the pore itself or to the surrounding lipids. Alternatively, the organic pore can be placed inside a larger solid state nanopore such as can be made in silicon nitride, and the plasmonic structure (e.g. metallic moiety) positioned such that MEF or SERS is optimized for those molecules or parts of molecules within the organic pore. Alternatively, an organic pore could be placed inside a plasmonic structure such as a photonic nanocavity (see FIGS. 5 and 6). The advantages of this method include the well-characterised behavior of single molecules induced to pass through such a pore, the small and highly reproducible pore diameter an organic pore allows, and the low cost of producing such organic pores.

The use of a solid state nanopore allows for control over the pore diameter and for nanopositioning plasmonic structures such that MEF or SERS is optimised. Ideally photon emission can be further controlled by means of a waveguide. This would allow for more efficient photon detection and higher detection speeds.

Figure 7:
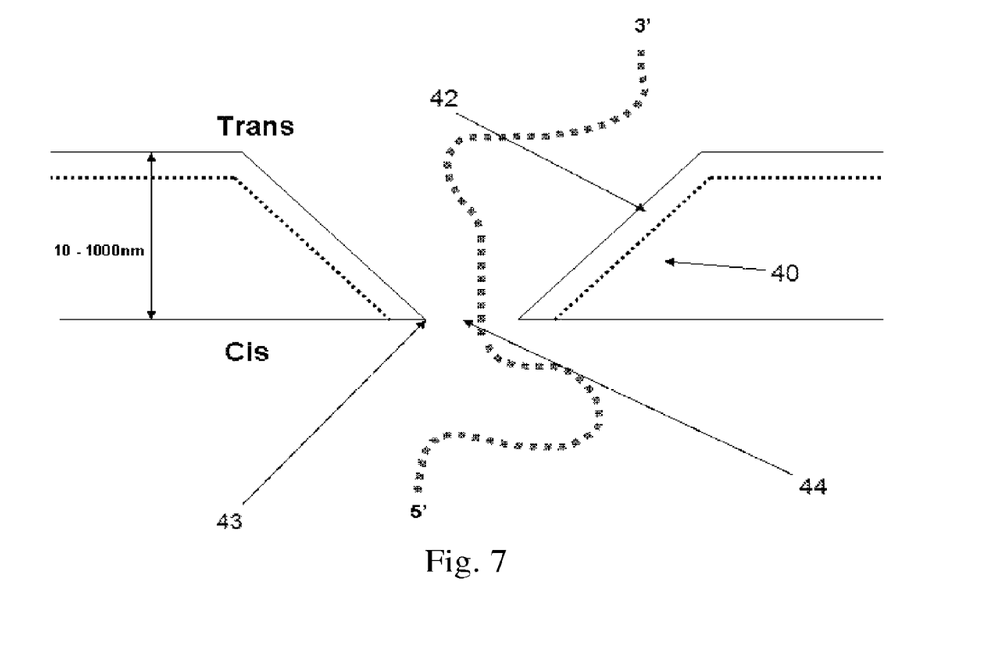

A third general method of construction is to allow for a random distribution of highly localised EMFs such that the field intensity at any given point on a porous surface is not known and to allow for the single molecule to pass through this surface at a controlled speed but uncontrolled location (FIG. 7). This has a tremendous advantage over the other two methods in that as neither the location nor the distribution of either the EMFs or the single molecules are precisely controlled, the ease with which such a device can be constructed is correspondingly greater. A method controlling the speed of the single molecules at the intersection of a 20 nm pore and a surface containing randomly distributed EMFs is described below. This method has the advantage in that it is intrinsically multiplexed. Even if the fluorescence produced by a single molecule passing through an EMF is such that only one molecule can be detected per second, the device can be multiplexed such that several hundred or thousand or million pores are in operation at once.

Figure 1:
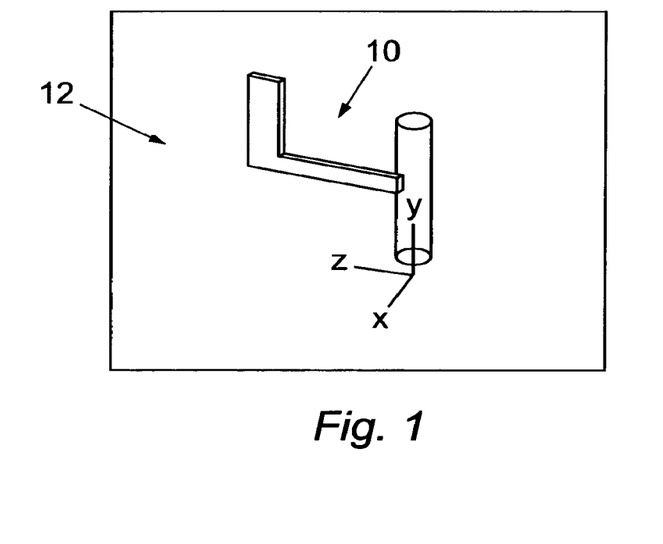
FIG. 1 shows a pore and electrode suitable for use in the present invention.
Figure 2:
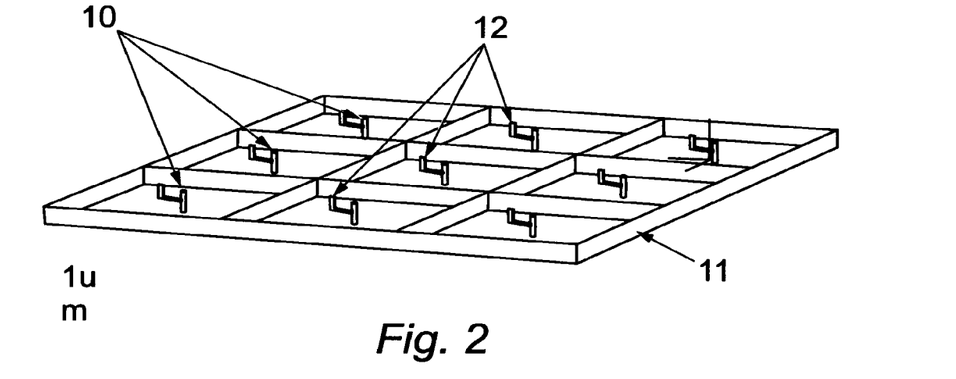
FIG. 2 shows a substrate comprising pores and electrodes.
Figure 3:
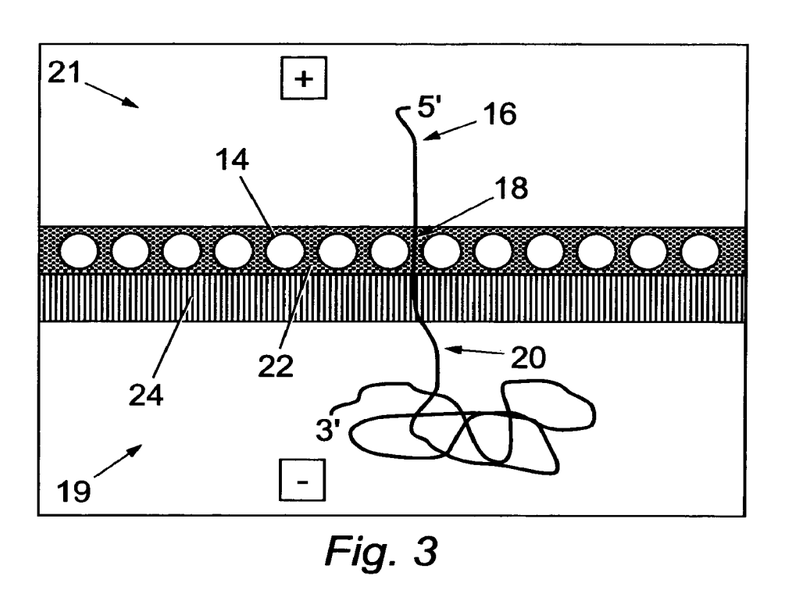
FIG. 3 shows a schematic representation of aspects of an apparatus according to the present invention.
Figure 4:
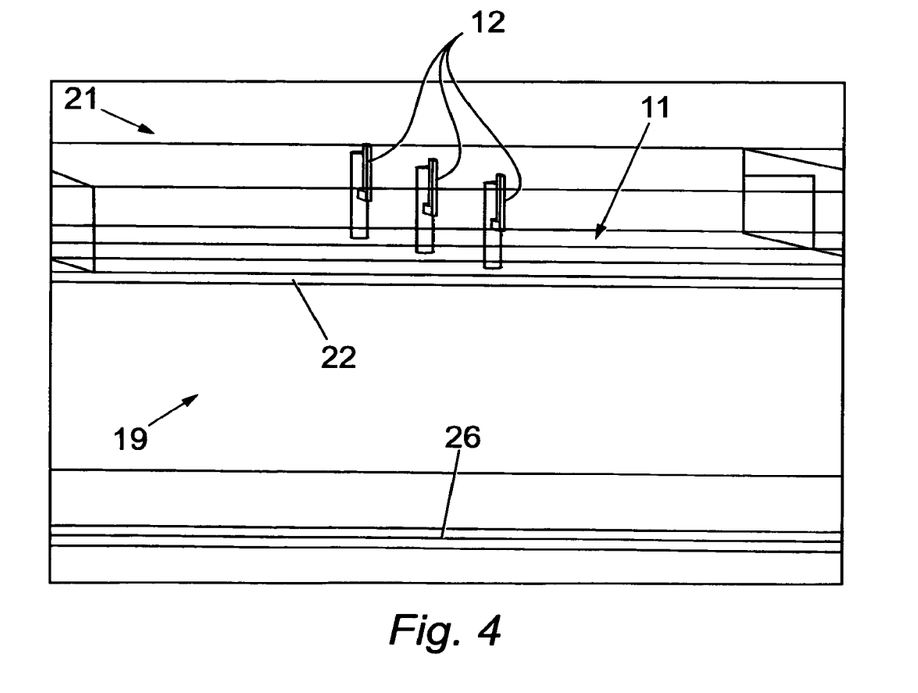
FIG. 4 shows a schematic representation of an embodiment of an apparatus according to the present invention.

Method for Construction of an Apparatus According to the Present Invention and Performing Sequencing An apparatus according to the present invention comprises the following:

- A first reservoir 19 capable of holding several µL of solution and containing an electrode 26 embedded in its bottom surface;
- A layer of silicon (substrate) 11 with an array of nanopores 10, which are 20 nm in diameter and which are spaced 1 µm apart etched in its surface. Electrodes 12 are embedded in the silicon layer 11 such that each 20 nm diameter pore 10 contains an electrode 12, and each electrode 12 is connected to a voltage supply with a high skew rate (not shown);
- A porous membrane 22, on which a regular array of gold nanoparticles 14 are deposited, is bonded to the silicon layer. The gold nanoparticles 14 are of known size and geometry, and when excited at the appropriate frequency, produce an EMF;
- A gel 24 such as agarose or polyacrylamide is applied to the membrane 22 having an average pore size such that when ssDNA 20 is induced to migrate through the gel 22 it will adopt an approximately linear conformation. This forms the control means in the present embodiment of the invention;
- A second reservoir 21 is provided on the other side of the substrate 22 into which a molecule will pass after having travelled through the pore;
- An array of voltage modulators (not shown) with a high skew rate are linked to a sensitive photon detector such as an avalanche photodiode (not shown);
- A photon detector such as an avalanche photodiode (not shown) is provided;
- A means of controlling an array of voltage supplies based on input from a photon detector (not shown) is provided;
- A laser of a frequency capable of inducing plasmon resonance in the metal colloids of known size and geometry (not shown) is provided.

Method of Operation to Perform Sequencing

DNA is labelled via PCR as previously described such that all of two bases (C and A or G and T) in a given strand of ssDNA are fluorescently labelled with fluorescent labels which have a maximum emission near, but preferably slightly red shifted in relation to, the plasmon resonant frequency of the metal colloids 14 being used.

The labelled ssDNA is then placed in the first reservoir 19. The membrane 22 coated with a nanoporous gel 24 and containing an approximately even distribution of gold nanoparticles 14 such that the spacing between them varies randomly between 1 nm and 100 nm is placed above the first reservoir 19. The silicon layer 11 is then placed on the membrane 22 and the entire assembly can be immersed in a conducting solution. A positive charge is then given to the electrodes 12 inside the 20 nm pores 10 such that ssDNA 20 will be induced to migrate through the second reservoir 21 into the gel 24, pass through the gel 24 in linear conformation and pass the gold nanoparticle 14 array emitting photons as they pass through the EMF produced by the plasmon resonance. As the fluorescently labelled random primers were used in the PCR reaction, the first photon emission will be produced by either the 5' or 3' primer. The photon emission obtained from the primer will immediately indicate the speed at which the ssDNA 20 fragment can be induced to migrate through the EMF and a clear signal still be obtained. As the positioning of the ssDNA 20 in relation to the gold spheres 14 will be different inside each of the 20 nm pores 10 for every ssDNA fragment 20, there will be an optimal voltage which can be applied to each pore 10 at any given time. As outlined above, a distance map containing the distances relative to each other and to the known primers can be created from the photon emission data. This data can then be assembled into a complete genome sequence.

Additional Methods for Preparation of a Substrate and Performing Sequencing

There are many way in which a suitable substrate can be produced using nanotechnological techniques. The following describes two possible ways and the manner in which a sequencing protocol would be preformed.

EXAMPLE 1

Figure 5:
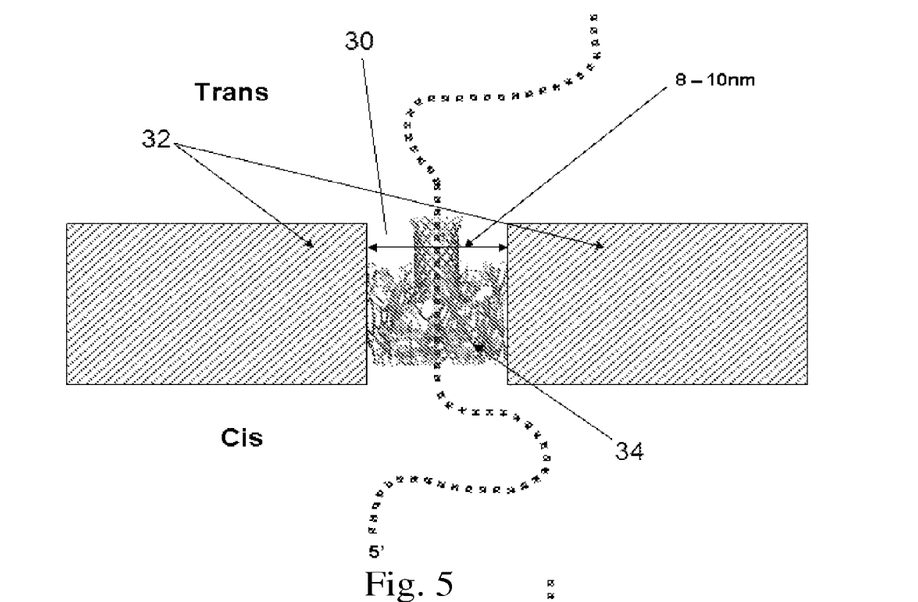
FIGS. 5 to 7 show schematic representations of alternative structures of the substrate.
Figure 6:
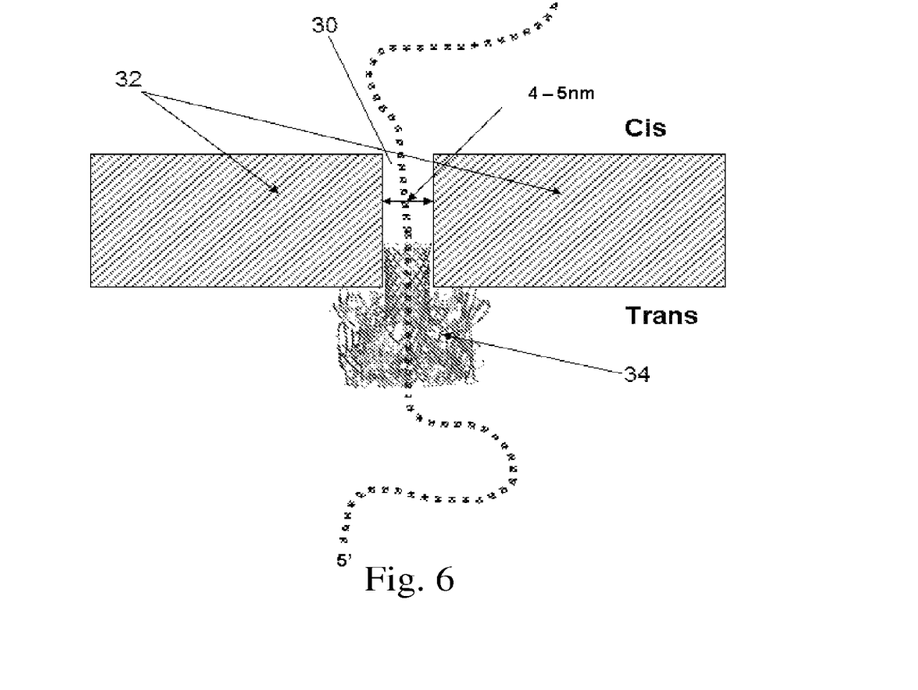

Organic Pore in a Plasmonic Nanocavity (as Illustrated in FIGS. 5 and 6)

1) An array of plasmonic structures such as photonic nanocavities 30 are constructed of a suitable material 32 as described in [4], the nanocavities having an inside diameter of 8 to 10 nm as in FIG. 5, or having an inside diameter of 4 to 5 nm as in FIG. 6.

2) An organic pore 34 such as a-haemolysin is then positioned inside these plasmonic structures by means suggested in [13] such that the organic pores 34 are spaced approximately 1 µm apart.

3) The plasmon resonance wavelength of these nanocavities 30 is then precisely determined and a laser and fluorescent dye spectra are chosen to correspond with the defined plasmon resonance. The fluorescent dye spectra should be slightly redshifted (20 to 150 meV) from the peak of plasmon resonance.

4) Electrolytic transport through the organic nanopore 34 is carried out as described in [10].

5) Photon emission from the fluorescent labels is detected using an avalanche photodiode detection system well-known in the art.

6) After extracting DNA from a chosen genetic source, ssDNA is fluorescently labelled using PCR and random primers such as are used in whole genome amplification. Of the four nucleotides present in the PCR reaction, one will be present only in its dye-modified form, ensuring high density fluorescent labelling of the chosen nucleotide. In order to ensure high density labelling with long read lengths, several fluorescent dyes may have to be tested with various polymerases as described in [7].

7) This PCR reaction is then carried out for the remaining three nucleotides such that four PCR reactions will have been carried out, resulting in four samples containing DNA fluorescently labelled at all of the C, T, G, and A nucleotides respectively.

8) Immediately before the DNA is passed through the sequencing device, the PCR reactions are denatured as is well known in the art, to allow labelled ssDNA to pass through the nanopores 34.

9) One denatured PCR reaction at a time is allowed to pass through the nanopore 34.

10) Photon emission from the dye molecules is obtained by an APD accurate to one millionth of a second. The timings of these bursts of photon emission are normalised with what is known regarding translocation of ssDNA through a pore and several thousand or million distance maps are created revealing the spacing between identical nucleotides.

11) These distance maps are then reassembled first into four completely re-assembled sequences of identical nucleotides, and composited into a complete genome sequence.

EXAMPLE 2

Synthetic Nanopore (as Illustrated in FIG. 7)

1) An array of conical nanopores having an inside radius at the tip of 30 nm or less are etched in a semiconducting silicon nitride or conducting metal membrane 40 using electron beam lithography well known in the art. These nanopores are spaced 1 µm apart. The etched silicon membrane is installed on a stage as described in [11] and placed in electroplating liquid in a small Teflon tube (2 mm diameter), which operates as an electroplating bath. TEMPEREX 8400 (Tanaka Kikinzoku) including 1.17% (w/w) KAu(CN)2 is used as the electroplating liquid at room temperature. A gold wire (0.5 mm diameter) was immersed in the solution as a counterelectrode. A bias voltage of 1.4 to 1.5 V is then applied to the initial electrodes relative to the counterelectrode in the system. This is followed by the electrodeposition of gold on the surface of the initial electrodes. Typically, an inducing current of 0.2 mA allows an electroplating rate of 1 A°/s at room temperature.

2) A layer of gold 42 is then deposited using electrodeposition as described in [11] to produce a pore 1.5 to 2.5 nm in diameter. When excited by an incident wave of the appropriate wavelength, this structure will produce a highly localised EMF concentrated at the tip of the conical pore [12].

3) As the labelled ssDNA is induced to migrate through the pore 44 by electrophoresis individual labels come into contact with the edge 43 of the pore 44. As the EMF is highly localised around the pore's 44 edge, as a fluorescent label passes through the field, photon emission would be expected. Contact between the gold surface at the pore's 44 tip and the fluorescently labelled ssDNA, however, induces fluorescent quenching. As the labelled ssDNA continues to move past the tip of the pore and into the channel, the channel expands. This expansion eliminates contact with the surface of the plasmonic structure and the resultant fluorescent quenching.

4) The plasmonic resonance wavelength of these electroplated conical pores 44 is then precisely determined and a laser and fluorescent dye spectra are chosen to correspond with the defined plasmon resonance. The fluorescent dye spectra should be slightly redshifted (20 to 150 meV) from the peak plasmon resonance.

5) Electrolytic transport through the conical nanopore 44 is carried out as described in [8,9].

6) Photon emission from the fluorescent labels is detected using an avalanche photodiode detection system well-known in the art.

7) After extracting DNA from a chosen genetic source, ssDNA is fluorescently labelled using PCR and random primers such as are used in whole genome amplification. Of the four nucleotides present in the PCR reaction, one will be present only in its dye-modified form, ensuring high density fluorescent labelling of the chosen nucleotide. In order to ensure high density labelling with long read lengths, several fluorescent dyes may have to be tested with various polymerases as described in [7].

8) This PCR reaction is then carried out for the remaining three nucleotides such that four PCR reactions will have been carried out, resulting in four samples containing DNA fluorescently labelled at all of the C, T, G, and A nucleotides respectively.

9) Immediately before the DNA is passed through the sequencing device, the PCR reactions are denatured as is well known in the art, to allow labelled ssDNA to pass through the nanopores 44.

10) One denatured PCR reaction at a time is allowed to pass through the nanopore 44.

11) Photon emission from the dye molecules is obtained by an APD accurate to one millionth of a second. The timings of these bursts of photon emission are normalised with what is known regarding translocation of ssDNA through a pore 44 and several thousand or million distance maps are created revealing the spacing between identical nucleotides.

12) These distance maps are then reassembled first into four completely re-assembled sequences of identical nucleotides, and composited into a complete genome sequence.

REFERENCES

[1] Fu, Yi, Lakowicz; Joseph R., "Single molecule studies of enhanced fluorescence on silver island films", Plasmonics, Vol. 2, No. 1, 2007.
[2] Nakamura, Toshihiro; Hayashi, Shinji, "Enhancement of dye fluorescence by gold nanoparticles: Analysis of Particle Size Dependence", Japanese Journal of Applied Physics, Vol. 44, No. 9A, pp. 6833-6837, 2005.
[3] Pompa, P. P. et al, "Metal enhanced fluorescence of colloidal nanocrystals with nanoscale control", Nature, published online 3 November, 2006.
[4] Netti, M. Caterina et al, "Confined plasmons in gold photonic nanocavities", Advanced Materials, Vol. 13, No. 18, 2001.
[5] Aizpurua, J. et al, "Optical properties of gold nanorings", Physics Review Letters, Vol. 90, No. 5, 2003.
[6] Kucheyev, S. O. et al, "Surface-enhanced Raman scattering on nanoporous Au", Applied Physics Letters, Vol. 89, 2006.
[7] Taurai, Tasara et al, "Incorporation of reporter molecule-labelled nucleotides by DNA polymerases. II. High-density labelling of natural DNA", Nucleic Acids Research, Vol. 31, No. 10, 2003.
[8] Heng, J. B. et al, "The Electromechanics of DNA in a synthetic nanopore", Biophysical Journal, Vol. 90, February 2006.
[9] Ho, Chuen et al, "Electrolytic transport through a synthetic nanometer-diameter Pore", PNAS, Vol. 102, No. 30, 2005.
[10] Astier, Yann; Braha, Orit; Bayley, Hagan, "Towards single molecule DNA sequencing", Journal of American Chemical Society, Vol. 128, 2006.
[11] Kashimura, Yoshiaki et al, "Fabrication of nano-gap electrodes using electroplating technique" Thin Solid Films 438-439, 2003.
[12] Downes, Andrew; Salter, Donald; Elfick, Alistair, "Simulations of atomic resolution tip-enhanced optical microscopy" OPTICS EXPRESS, Vol. 14, No. 23, 2006.
[13] Bayley, Hagan; Cremer, Paul S., "Stochastic sensors inspired by biology", NATURE, Vol. 413, September 2001.

The invention claimed is:

1. A method for analyzing a DNA molecule, the method comprising:
    providing a first reservoir and a second reservoir separated by a substrate, wherein the substrate includes a nanopore, the nanopore includes at least one metallic nanoparticle in an area facing the second reservoir, and the at least one metallic nanoparticle is capable of producing plasmon resonance;
    inducing a fluorescently labeled single-stranded DNA molecule into the first reservoir;
    inducing the fluorescently labeled single-stranded DNA molecule to move from the first reservoir to the second reservoir via the nanopore and in close proximity to the at least one metallic nanoparticle;

inducing particle plasmon resonance in the at least one metallic nanoparticle in the area facing the second reservoir, the at least one metallic nanoparticle producing, by the particle plasmon resonance, a localized electromagnetic field at the area of the nanopore facing the second reservoir;

detecting fluorescence produced by the interaction of (i) the localized electromagnetic field produced by the at least one metallic nanoparticle at the area of the nanopore facing the second reservoir and (ii) the fluorescently labeled single-stranded DNA molecule moving into the second reservoir via the nanopore; and analyzing the fluorescently labeled single-stranded DNA molecule based on the detected fluorescence.

2. The method according to claim 1 wherein the fluorescently labeled single-stranded DNA molecule is fluorescently labeled with a label including one of Rose Bengal, $C_5$-maleimide, $C_2$-maleimide, Rhodamine Red, $C_2$-meleimide, and Rhodamine Green.

3. The method according to claim 2 wherein the label has an emission peak at slightly lower energy than the localized surface plasmon resonance peak of the metallic nanoparticle.

4. The method according to claim 1, wherein the nanopore has a diameter of 0.5-100 nm.

5. The method according to claim 4, wherein the nanopore has a diameter of 1-50 nm.

6. The method according to claim 1, wherein all of one or more of the four bases in the fluorescently labeled single-stranded DNA molecule is fluorescently labeled.

7. The method according to claim 1, wherein the at least one metallic nanoparticle includes gold, silver, copper, or aluminum.

8. The method according to claim 1, wherein the at least one metallic nanoparticle is substantially spherical in shape.

9. The method according to claim 8 wherein the at least one metallic nanoparticle is made of gold.

10. The method according to claim 8 wherein the at least one metallic nanoparticle has a diameter from 50 nm to 150 nm.

11. The method according to claim 1 wherein the substrate includes an array of nanopores and the at least one metallic nanoparticle is a plurality of metallic nanoparticles arranged in an array corresponding to the array of nanopores.

12. The method according to claim 1 wherein the substrate and nanopore comprise an organic pore in a larger solid-state nanopore with the at least one metallic nanoparticle positioned such that metal enhanced fluorescence is optimized for that part of the single-stranded DNA molecule within the organic pore.

13. The method according to claim 12 wherein the organic pore is made of α-haemolysin.

14. The method according to claim 1 wherein said analyzing includes generating a distance map of labeled nucleotides comprising the single-stranded DNA molecule.

15. The method according to claim 14
wherein the single-stranded DNA molecule is a single-stranded fragment of DNA from a whole genome, and
wherein said method further comprises assembling the distance maps from different single-strand DNA fragments using genome assembly software to generate the sequence of the whole genome.

* * * * *